United States Patent [19]

Kleinerman

[11] Patent Number: 5,090,818
[45] Date of Patent: * Feb. 25, 1992

[54] FIBER OPTIC SYSTEMS FOR SENSING TEMPERATURE AND OTHER PHYSICAL VARIABLES

[76] Inventor: Marcos Y. Kleinerman, 24 Jerome St., Southbridge, Mass. 01550

[ * ] Notice: The portion of the term of this patent subsequent to Nov. 24, 2004 has been disclaimed.

[21] Appl. No.: 516,532

[22] Filed: Apr. 30, 1990

Related U.S. Application Data

[60] Division of Ser. No. 711,062, Mar. 12, 1985, Pat. No. 5,004,913, which is a continuation-in-part of Ser. No. 608,932, May 14, 1984, Pat. No. 4,708,494, which is a continuation of Ser. No. 405,732, Aug. 6, 1982, abandoned.

[51] Int. Cl.⁵ .................. G01K 11/20; G01K 13/00; G01J 5/08
[52] U.S. Cl. .................................. 374/131; 374/161; 374/142; 356/44; 250/227.18; 250/227.23; 250/458.1
[58] Field of Search ............... 374/161, 131, 159, 121, 374/137, 142, 143; 356/44; 250/458.1, 227.23, 227.18; 252/301.33

[56] References Cited

U.S. PATENT DOCUMENTS

| | | | |
|---|---|---|---|
| Re. 31,832 | 2/1985 | Samulski | 374/131 |
| 4,075,493 | 2/1978 | Wickersheim | 374/159 |
| 4,374,328 | 2/1983 | Tekippe et al. | 250/461.1 |
| 4,376,890 | 3/1983 | Engström et al. | 250/227.3 |
| 4,378,496 | 3/1983 | BrogÅrdh et al. | 250/227.23 |
| 4,409,476 | 10/1983 | Lögfren et al. | 374/161 |
| 4,437,772 | 3/1984 | Samulski | 374/131 |
| 4,455,741 | 6/1984 | Kolodner | 374/161 |
| 4,539,473 | 9/1985 | BrogÅrdh et al. | 374/161 |
| 4,550,256 | 10/1985 | Berkstresser et al. | 250/486.1 |
| 4,562,348 | 12/1985 | BrogÅrdh et al. | 250/227.21 |
| 4,569,570 | 2/1986 | BrogÅrdh et al. | 250/486.1 |
| 4,607,158 | 8/1986 | Ovren | 250/216 |
| 4,626,110 | 12/1986 | Wickersheim et al. | 374/161 |
| 4,648,094 | 3/1987 | McCollum et al. | 372/41 |
| 4,652,143 | 3/1987 | Wickersheim et al. | 374/161 |
| 4,708,494 | 11/1987 | Kelinerman | 374/131 |
| 4,729,668 | 3/1988 | Angel et al. | 374/161 |
| 4,752,141 | 6/1988 | Sun et al. | 374/161 |
| 4,768,886 | 9/1988 | Hirschfeld et al. | 374/161 |
| 4,776,827 | 10/1988 | Greaves | 374/161 |
| 4,806,757 | 2/1989 | Kano et al. | 250/327.2 |
| 4,859,079 | 8/1989 | Wickersheim et al. | 374/161 |
| 4,880,972 | 11/1989 | BrogÅrdh et al. | 374/161 |

FOREIGN PATENT DOCUMENTS 0146522  6/1985  European Pat. Off. ............ 374/161

OTHER PUBLICATIONS

Lengyel, B. A., "Lasers", 2nd Edition, Wiley-Interscience, New York (1971), Chapter 4, pp. 105-132 (Sections 4.1 to 4.3).

Sholes, R. R., et al., "Fluorescent Decay Thermometer with Biological Applications", Rev. Sci. Instrum., vol. 51, No. 7 (Jul. 1980).

Wickersheim, K. A., et al., "Recent Advances in Optical Temperature Measurement", Industrial Research/Development (Dec. 1979).

*Primary Examiner*—Allan N. Shoap
*Assistant Examiner*—Diego F. F. Gutierrez

[57] ABSTRACT

The invention is drawn to methods and devices which allow the simultaneous optical measurement of temperature and another physical parameter using a single probe, a single interrogating light source and a single photodetector. The invention also allows the use of a single probe for meausring temperature in two independent physical modes, using a single interrogating light source and a single photodetector. The single probe includes a photoluminescent material having luminescent centers which when excited with transient interrogating light of a wavelength within a predetermined spectral range emit luminescence light from two excited electronic energy levels, one of them being higher than the other and having a higher rate of luminescence decay than the other level, and wherein the relative intensities of the luminescence light emitted from each of the two excited energy levels vary as a function of the probe temperature. The temperature measured by the probe is determined by measuring the decay time of the luminescence emitted from the probe.

11 Claims, 5 Drawing Sheets

FIBER OPTIC SYSTEMS FOR SENSING TEMPERATURE AND OTHER PHYSICAL VARIABLES

CROSS-REFERENCE TO RELATED APPLICATIONS

This is a divisional application of co-pending application Ser. No. 711,062 filed Mar. 12, 1985, now U.S. Pat. No. 5,004,913, which in turn is a continuation-in-part of application Ser. No. 608,932 filed May 14, 1984, now U.S. Pat. No. 4,708,494, which in turn is a continuation of application Ser. No. 405,732 filed Aug. 6, 1982, now abandoned.

BACKGROUND OF THE INVENTION

The present invention relates to methods and devices for the measurement of physical parameters using a class of optical probes which permit the measurement of temperature by at least two physically independent optical methods, or the measurement of temperature in addition to at least another physical parameter, using a single optical probe, a single interrogating light source and a single photodetector, in conjunction with fiber optic techniques.

Prior art methods and devices for measuring temperature include the use of probes made of materials having temperature-dependent photo-luminescence properties. One of the earliest systems was described in U.S. Pat. No. 2,551,650 of Urbach, and used a photo-luminescent material the luminescence intensity of which was quenched appreciably with an increase of temperature. Luminescence quenching is usually associated with a decrease of the luminescence decay time of the material following excitation of its luminescence by pulsed or oscillatory light of wavelengths within an electronic absorption band characteristic of the material. Since the measurement of a luminescence decay time is usually more accurate and reliable than the measurement of a luminescence intensity (especially in the absence of intensity referencing), some recent temperature measurement techniques using photo-luminescent probes have used the temperature-dependent luminescence decay time as temperature indicator. These decay time techniques were used in a plurality of fiber optic temperature measuring techniques, including among others those described in U.S. Pat. Nos. 4,223,226 and 4,245,507 and in a publication by J. S. McCormack (*Electronics Letters* 17, 630 [1981]). These prior art techniques have, however, a serious disadvantage: As temperature increases, the signal strength and, hence, the measurement accuracy, decrease. This limits severely the temperature range of operation of probes which have a temperature coefficient of decay time of the order of one percent or better, so a wide temperature range can be achieved only with probes having a significantly lower decay time coefficient and, hence, a significantly lower sensitivity and accuracy.

In many situations encountered in industry, it is necessary to measure a physical parameter, for example pressure, under temperature-varying conditions. Temperature variations may affect the performance of the pressure sensor, so it is often necessary to measure the temperature of the pressure sensor in order to introduce the appropriate correction factors for processing the pressure readings. This usually requires a temperature measuring device in addition to the pressure sensor, which increases the complexity of the instrument.

OBJECTS OF THE INVENTION

It is an object of the present invention to provide fiber optic temperature measuring systems using probes characterized by easily measurable luminescence decay times which vary as a sensitive function of temperature, but without the disadvantage of significant luminescence quenching.

It is another object of the present invention to provide fiber optic methods and devices using a single probe for measuring temperature in addition to another physical parameter like force or displacement.

Yet another object of this invention is to provide self-checking fiber optic thermometers.

Other objects of the present invention will become apparent from the description provided in the following sections of the specification.

The invention accordingly comprises the methods, materials, apparatuses and systems, together with their steps, parts, elements and interrelationships that are exemplified in the following disclosure, the scope of which will be indicated in the appended claims.

SUMMARY OF THE INVENTION

The objects of this invention are accomplished by the use of probes made of luminescent materials characterized by a luminescence quantum efficiency which remains essentially invariant or varies only minimally over the temperature range of operation of the probe, but have at least one other photo-luminescence property which is a sensitive function of temperature over the same range. Such combination of properties permits the construction of sensor systems in which a single optical probe can be used for the following measurements:

a) simultaneous measurement of temperature and another physical parameter, using in a preferred embodiment a single light source and a single photodetector; or b) simultaneous measurement of two physically independent temperature indicators, using in a preferred embodiment a single light source and a single photodetector to provide self-checking operation of the sensor system.

The invention teaches how such systems can be constructed and how they can be operated, beginning with an explanation of how one can measure temperature with luminescent probes having a luminescence quantum efficiency which remains essentially invariant over at least a relatively large part of their useable temperature range.

DEFINITIONS

Within the context of this application, I am using the following definitions:

Light: optical radiation, whether or not visible, which is absorbed, emitted and/or otherwise modified by an optical probe or device.

Occupancy number of an energy level: the fraction of the total number of molecules of a probe material occupying said energy level.

Vibronic material: any luminescent material whose molecular electronic ground energy level comprises a plurality of vibrational sublevels with energies higher that that of the lowest occupied level of the material, said vibrational sublevels being so distributed as to cover an essentially continuous wide band of energies.

Vibronic level: a vibrational sublevel of the electronic ground level of a vibronic material, having an occupancy number which increases with increasing temperature.

Physical variable: any physical property whose magnitude can change. Examples: temperature, pressure, flow rate, position, liquid level, and the like.

Physical parameter: physical variable.

Interrogating light: illuminating light injected into an optical probe for the physical variable.

Excitation light: illuminating light which can generate luminescence in a luminescent material.

Light beam: light being propagated through an optical system, including optical fibers, regardless of degree of divergence.

Luminescence decay time (symbol: $\tau$): the time after the cessation of the excitation light at which the intensity of the luminescence light decreases from an initial intensity $I_0$ to the intensity $I_0/e$, the value of e being approximately 2.718.

DETAILED DESCRIPTION OF THE INVENTION

1.0 Temperature Sensing Based on the Direct Measurement of Thermally Activated Light Absorption in Luminescent Materials The technique described in this section uses photo-luminescent probes, but does not require any photo-luminescence property which varies with temperature over the temperature range being measured, and can be implemented with probes made of virtually any solid or liquid photo-luminescent material. The probes are operated according to the principles described and illustrated with reference to FIG. 1. The analysis that follows is deliberately oversimplified to emphasize the aspects most relevant to the invention. The quantitative relationships may not be followed rigorously in all practical systems.

Figure 1:
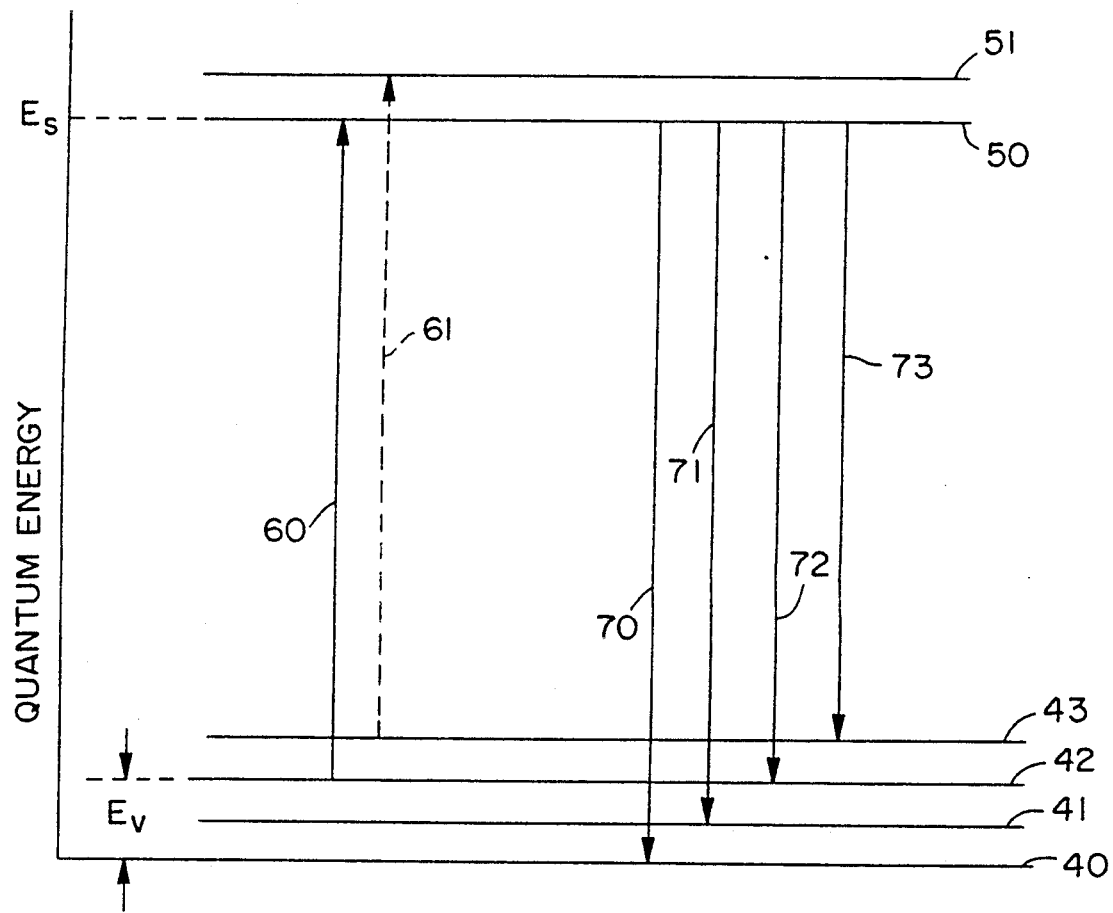
FIG. 1 is a simplified molecular energy diagram illustrating a temperature-dependent optical absorption process and luminescence conversion of the absorbed light in most luminescent materials.

FIG. 1 shows an electronic energy level diagram which at least qualitatively describes, at the molecular level, most luminescent materials. The luminescent material has a ground electronic level comprising vibrational sublevels 40, 41, 42, 43 and other sublevels which, for the sake of simplicity, are not shown. These materials are referred herein as "vibronic" materials. The lowest excited electronic energy level comprises vibrational sublevels 50, 51, and other vibrational sublevels not shown. The vertical arrowed line 60 represents an optical electronic transition, produced by the absorbed excitation light from level 42 to vibrational sublevel 50, which have fixed energies $E_v$ and $E_s$, respectively, relative to level 40. The length of line 60 corresponds to the photon energy of the optical transition and, hence, to the specific wavelength $\lambda_v$ of the excitation light. This wavelength obeys the relation $\lambda_v = hc/(E_s - E_v)$, where h is Planck's constant and c is the velocity of light in a vacuum. The wavelength $\lambda_v$ can excite only molecules occupying vibronic level 42 and, to a smaller extent, molecules occupying slightly higher levels, the excitation of which is represented by the dotted vertical line 61. Luminescence emission occurs from sublevel 50 to the vibronic levels of the ground electronic level., said emission represented by lines 70, 71, 72 and 73. As shown in FIG. 1, a considerable spectral portion of the emission occurs at photon energies higher (and wavelengths shorter) than that of the excitation light, and is commonly referred to as anti-Stokes luminescence.

In practice the vibronic material is often used as a solid solution, glassy or crystalline, in a transparent host material, said solid material constituting the temperature probe. The concentration of the vibronic material and the dimension of the probe along the direction of the illuminating light are chosen so that the probe absorbs only a fraction $\alpha_v$ of the nearly monochromatic excitation light within the temperature range of operation, and transmits the rest. The absorbed fraction obeys the following relation:

$$\alpha_v = 1 - 10^{-\epsilon c_o d(N_{42}/N)} \quad (1)$$

where $\epsilon$ is the molar decadic absorption coefficient of the molecules occupying the vibronic level 42;

$c_o$ is the total molar concentration of the vibronic material;

d is the length of the sensor in the direction of the incident excitation light;

$N_{42}$ is the number of molecules of the vibronic material occupying vibronic level 42; and N is the total number of molecules of the vibronic material.

The ratio $N_{42}/N$ essentially follows the relation $$N_{42}/N = f^{-1} \cdot \exp(-E_v/kT) \quad (2)$$

where f is the so-called partition coefficient of the molecular system, k is the Boltzmann constant, and T is the absolute temperature. The expression $c_o \cdot f^{-1} \exp(-E_v/kT)$ is essentially the effective molar concentration of the molecules of the vibronic material occupying the vibronic level 42, and the quantity $10^{-\epsilon c_o d(N_{42}/N)}$ represents the fraction of the illuminating (interrogating) light which is transmitted by the probe, assuming no scattering and/or reflection losses, and equal to $(1 - \alpha_v)$. The ratio $E_v/k$ can be designated by the single constant $\beta$, for a given wavelength $\lambda_v$.

At optical densities no greater than 0.02, $\alpha_v$ is approximately given by $$\alpha_v \approx 2.3 \epsilon c_o df^{-1} \exp(-E_v/kT) \quad (3)$$

At optical densities greater than 0.02 the relationship between $\alpha_v$ and the Boltzmann factor $\exp(-E_v/kT)$ becomes less linear, but equations (1) and (2) are still valid, and the method can be used at high, low or intermediate optical densities.

The luminescence intensity $I_f$ generated by the light absorbed by the sensor obeys the relation $$I_f = P_o(\lambda_v/hc)\alpha_v\phi \text{ photons.sec}^{-1} \quad (4)$$

where $P_o$ is the radiant power, in watts, of the incident excitation light, and $\phi$ is the luminescence quantum efficiency of the vibronic material.

Probes made from materials having high $\phi$ values can produce large signal-to-noise ratios even with optical densities lower than 0.01, provided that the optical system has at least a moderately high collection efficiency for the generated luminescence. Such efficiency is easily obtainable with state-of-the-art fiber optic systems.

The sum of the light intensity absorbed and the light intensity transmitted by a clear medium is constant. It follows, therefore, that as the absorbed fraction $\alpha_v$ increases with an increase in temperature according to equation (3), the intensity of the transmitted fraction must decrease accordingly. Since, according to equation (4), the intensity of the luminescence light is proportional to $\alpha_v$, it follows that the ratio of the intensity of the luminescence light to that of the transmitted light increases with an increase in temperature, and the ratio can be used as a temperature indicator. The ratio eliminates or minimizes any sources of error associated with fluctuations of the intensity of the illuminating light and fiber or connector losses.

The temperature coefficient of the luminescence intensity follows approximately the relation $$(1/I_o)(dI_f/dT) = E_v/kT^2 = \beta/T^2 \quad (5)$$

where $I_o$ is the luminescence intensity at a chosen reference temperature. For example, a material with a value of $E_v$ of 1200 cm$^{-1}$ has a coefficient of about two percent per kelvin at a temperature of 295 K.

Equations (3) to (5) show that the method of the preceding paragraphs requires only a temperature-dependent change in the optical absorption coefficient of the luminescent probe material at wavelengths corresponding to photon energies lower than the energy $E_s$ of the excited emissive level. This property is shared by virtually all solid and liquid luminescent materials. The method does not require any temperature-dependent changes in the luminescence quantum efficiency, spectral distribution or decay time. Therefore, and in contrast to all other prior art methods, it can be implemented with most efficient luminescent materials.

Figure 2:
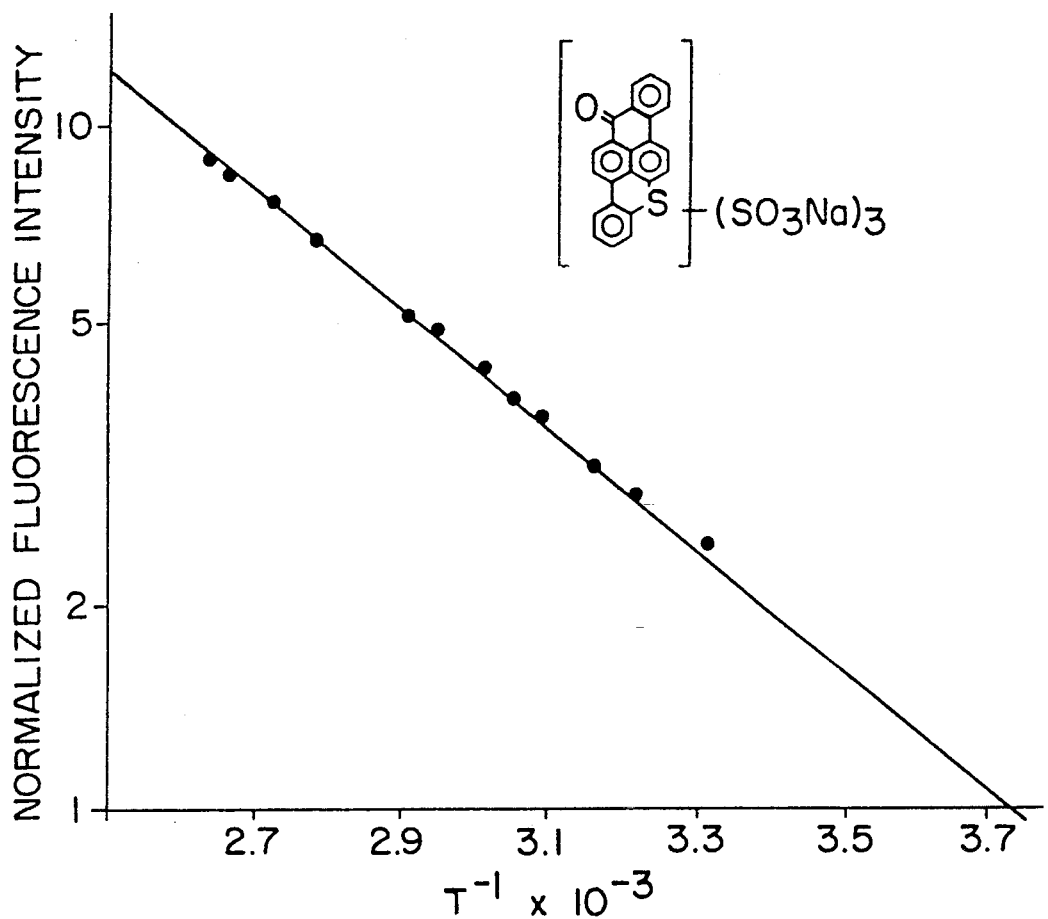
FIG. 2 shows the temperature dependence of the fluorescence intensity of a fluorescent material operated according to the principles illustrated in FIG. 1.

Experimental tests of equations (3) to (5) have been carried out, and the behavior predicted by the equations was verified. FIG. 2 shows actual normalized fluorescence intensity as a function of the inverse absolute temperature of a dimethyl sulfoxide (DMSO) solution of the dye represented by the formula

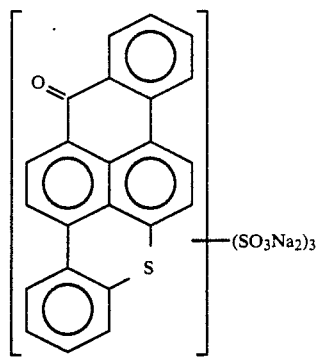

illuminated by a light beam from a helium-neon laser. The dye concentration was approximately $10^{-4}$ Molar, with a path length of 1 cm. The fluorescence intensity was monitored at a wavelength of 610 nanometers (nm), shorter than the laser beam wavelength of 632.8 nm. The superiority of this method of temperature measurement compared to that based on light transmission measurements becomes evident from the fact that over the temperature interval from about 300 K. (27° C.) to about 400 K. (127° C.) the light transmission of the dye solution varies by less than two percent, while the intensity ratio of fluorescence light to transmitted light varies by about an order of magnitude.

In the simplest embodiment of the method for temperature measurement according to this section, one only has to interrogate the luminescence probe material with light of a wavelength at which the probe material has a temperature-dependent absorption coefficient, and measure the intensity of the luminescence generated by the absorbed interrogating light. While the probe in the example of FIG. 2 is a liquid solution, solid probes, preferably in the form of optical fibers, can also be used in practical devices.

The above method can be implemented with any probe material having at least one energy level which can be thermally populated from the ground level to an extent that varies as a function of temperature. Such thermally populated level does not have to be a vibrational level or sublevel. It can be, for example, an electronic sublevel of the ground electronic level of a rare earth ion like Nd(III). A suitable probe may be an inorganic crystalline or glassy material doped with the rare earth ion.

Figure 3:
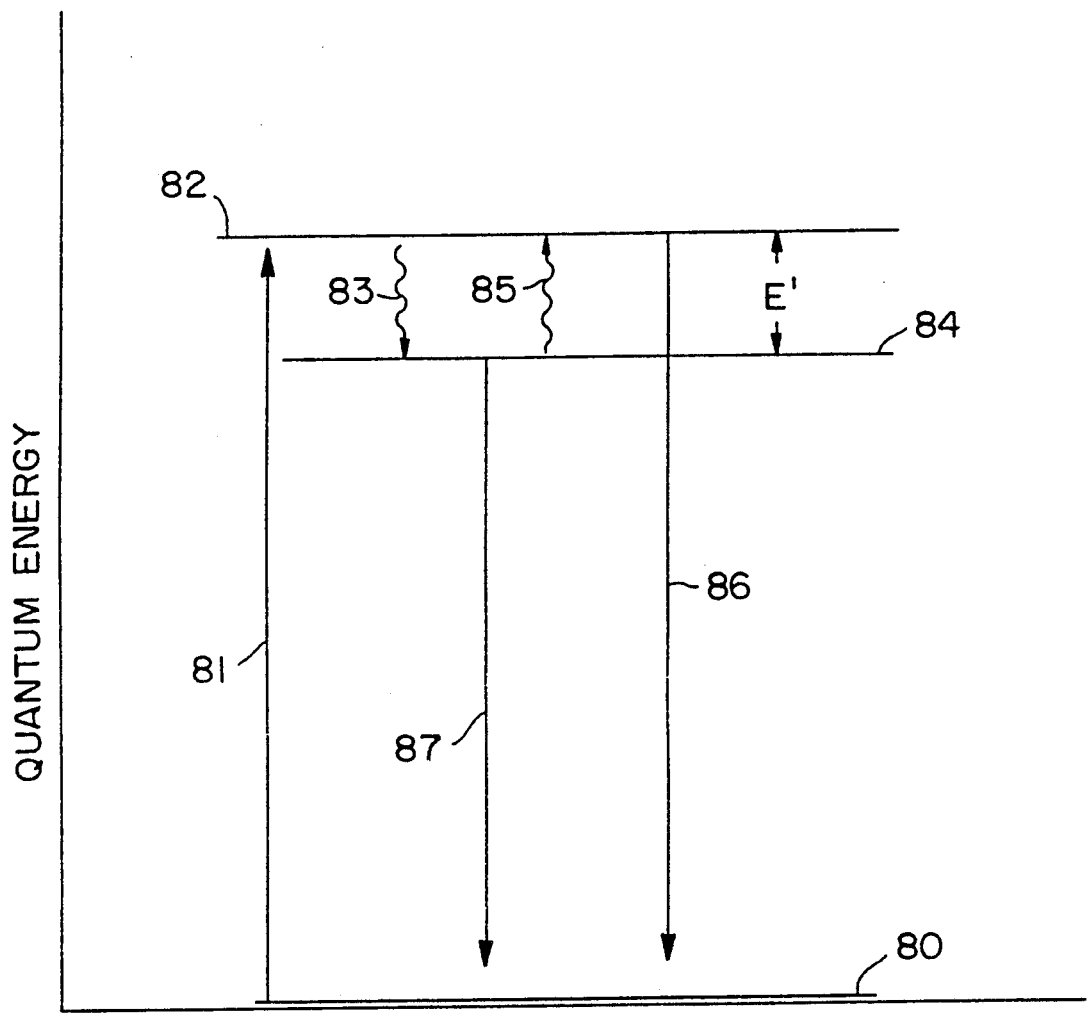
FIG. 3 is a schematic illustration of a temperature-dependent luminescence process determined by the thermal equilibrium between the occupancy numbers of two photo-luminescent levels of a class of luminescent materials.

2.0 Luminescent Materials Having two Emissive Levels with Temperature-Dependent Relative Populations Another preferred class of materials for the practice of this invention are so characterized that, when excited with light of a wavelength or wavelengths within an electronic absorption band characteristic of the material they emit, luminescence light from two excited levels the energies of which differ by the magnitude $E'$ and the relative occupancy numbers (populations) of which are a function of temperature. When excited with pulsed, oscillatory or other transient interrogating light, the intensity of the total luminescence emitted by said two levels has a decay time $\tau$ which varies as a sensitive function of temperature over a wide temperature range over which the quantum efficiency of said combined luminescence remains approximately constant. The temperature-dependent processes occurring in these materials are illustrated in FIG. 3, to which the following description applies. Molecules or ions of the luminescent material occupying the ground level 80 are excited by absorption of light, as depicted by the arrowed line 81, to the emissive level 82, from which they decay rapidly, via the radiationless process 83, to the long lived excited emissive level 84. A fraction of the number of the molecules or ions occupying level 84 are thermally excited, via radiationless step 85, to emissive level 82, the occupancy number (population) of which, relative to level 84, follows approximately the relation (in absence of level degeneracy), $$(N_{82})/(N_{84}) = \exp(-E'/kT) \qquad (6)$$

where $N_{82}$ and $N_{84}$ are the occupancy numbers (populations) of levels 82 and 84, respectively; k is the Boltzmann constant and E' is the magnitude of the energy difference between these two levels. Equation (6) expresses what is generally known as the "Boltzmann population factor" of the molecules of a system occupying an energy level with an energy E' relative to another, lower level. Levels 82 and 84 emit luminescence via radiative decays 86 and 87, with radiative rate constants $k_r'$ and $k_r$, respectively, with $k_r' >> k_r$. The ratio R' of the luminescence intensity emitted from level 82 to that from the lower level 84 follows approximately the relation (in the absence of level degeneracy)

$$R' = k_r'(N_{82})/k_r(N_{84}) \qquad (7)$$

which can also be written as $$R' = (k_r'/k_r)\exp(-E'/kT) \qquad (8)$$

Equations (7) and (8) show that the luminescence intensity from the higher level 82 increases, and R' increases exponentially, with increasing temperature. The value of R' can be measured by comparing the spectrally resolved luminescence intensities from each of the two emissive levels or, more conveniently, by measuring the decay time $\tau$ of the total luminescence of the material when excited with pulsed or AC-modulated interrogating light having a decay time much shorter than the luminescence decay time of the probe material. The luminescence decay time then decreases with increasing temperature according to the relation $$\tau = [1 + \exp(-E'/kT)]/[k_r + k_r'\exp(-E'/kT)] \qquad (9)$$

The temperature coefficient of $\tau$ depends on the temperature coefficient of R', and this is given by the relation $$(1/R_o')(dR'/dT) = (E'/kT^2) \qquad (10)$$

A measurement of $\tau$ gives, therefore, an indication of the probe temperature. The above equations imply a temperature-invariant quantum efficiency of the total luminescence emitted by the two levels 82 and 84, a condition which has been observed in some actual materials mentioned below. The preceding equations are applicable when the excitation light generates luminescence from only one kind of emissive centers in the probe. If this condition is not met the luminescence response may deviate somewhat from that predicted in the preceding equations. But such deviations do not affect the general validity and usefulness of this method of temperature measurement. In practice the probe is calibrated by recording a $\tau$ vs. temperature curve within the desired temperature range, with the aid of a precision reference thermometer, and storing said information in an electronic memory. Measurements made afterwards with the probe are compared automatically with the stored information by means of a microprocessor and/or other inexpensive electronic components, and the measured decay times are thus converted into reliable temperature readings.

There are numerous probe materials which can be used with this method, and they include most efficient luminescent materials having a relatively fast-decaying emissive electronic energy level above and in thermal equilibrium with a relatively slow-decaying emissive level. Examples are beryls, magnesium oxide and garnets, doped with chromium(III) or vanadium(II). Garnet crystals are widely used in electro-optic technology, especially the ubiquitous yttrium aluminium garnet (better known by its initials YAG), and other garnets often doped with Cr(III) for use as wavelength-tunable lasers.

One attractive advantage of these sensing materials, compared to prior art luminescent temperature probes based on a temperature-dependent luminescence decay time, is that the luminescence quantum efficiency does not degrade seriously over a wide temperature range over which the luminescence decay time may vary as a known, sensitive function of temperature by about an order of magnitude or more. For example, the luminescence decay time of emerald (a Cr(III)-doped beryl), varies from about 2 milliseconds at cryogenic temperatures to about 50 microseconds at about 130 degrees Celsius, a factor of about 40, with little or no change in luminescence quantum efficiency, unlike the prior art probes based on luminescence decay times, characterized by a large decrease in signal strength with increasing temperature. Cr(III)-doped YAG (Cr:YAG) behaves similarly, with a large temperature coefficient of its luminescence decay time over a wide temperature range in which the luminescence quantum efficiency remains high. The total luminescence quantum efficiency remains essentially constant over a relatively wide temperature range over which the luminescence decay time undergoes relatively large measurable changes. This characteristic allows these materials to be used in probes for self-checking optical thermometry, and/or for the simultaneous measurement of temperature and at least another physical parameter with a single probe. The arrangements used for such measurements are described in sections 3.0 to 5.0, below.

3.0 Self-checking Temperature Measuring Systems

If a single optical temperature probe could be operated in at least two independent modes, then a thermometer using that probe could be self-checking, that is, the temperature reading obtained from one mode of operation will agree with the temperature reading obtained from the other mode, if the device using the probe is functioning properly. The teachings of this invention permit self-checking operation of optical thermometers using a single luminescent probe. It has been pointed out already that the method for measuring temperature based on thermally activated light absorption and luminescence conversion of the absorbed light, as discussed in section 1.0 above, can be implemented with virtually any solid luminescent material. This method can be used with the luminescent materials subject of section 2.0, having a temperature-dependent luminescence decay time and a relatively high luminescence quantum efficiency over its temperature range of operation. It follows, then, that a temperature probe comprised of such material can be interrogated in two mutually independent modes, namely, (a) a temperature-dependent optical absorption coefficient at a wavelength $\lambda_\nu$, and (b) a temperature-dependent luminescence decay time. When interrogated with pulsed or AC-modulated light of wavelength $\lambda_\nu$ and a sufficiently short decay time injected into the probe, the probe will give two mutually independent temperature indicators: a time-averaged luminescence intensity $I_f$ proportional to the intensity of the interrogating light absorbed by the probe, and a temperature-dependent luminescence decay time $\tau$, which is independent of the intensity of the absorbed interrogating light. If the temperature measuring device using the probe is functioning correctly, then the temperature readings obtained from the two temperature indicators should agree with each other. Failure to so agree will immediately reveal a malfunction of the device. A single photodetector may be used for measuring simultaneously, or nearly simultaneously, both $I_f$ and $\tau$.

4.0 The Simultaneous Measurement of Temperature and Another Physical Variable with a Single Probe A serious problem in the industrial measurement of physical variables other than temperature is that the signals from most transducers can be affected by temperature changes. One way to deal with this problem is to add a temperature probe to the device used for measuring the variable of interest, and apply a temperature correction factor to the readings. The luminescent materials described in section 2.0 above, having a temperature-dependent luminescence decay time at essentially constant luminescence quantum efficiency, make it possible to measure both temperature and another physical parameter, for example pressure or another force, with a single probe.

Figure 4:
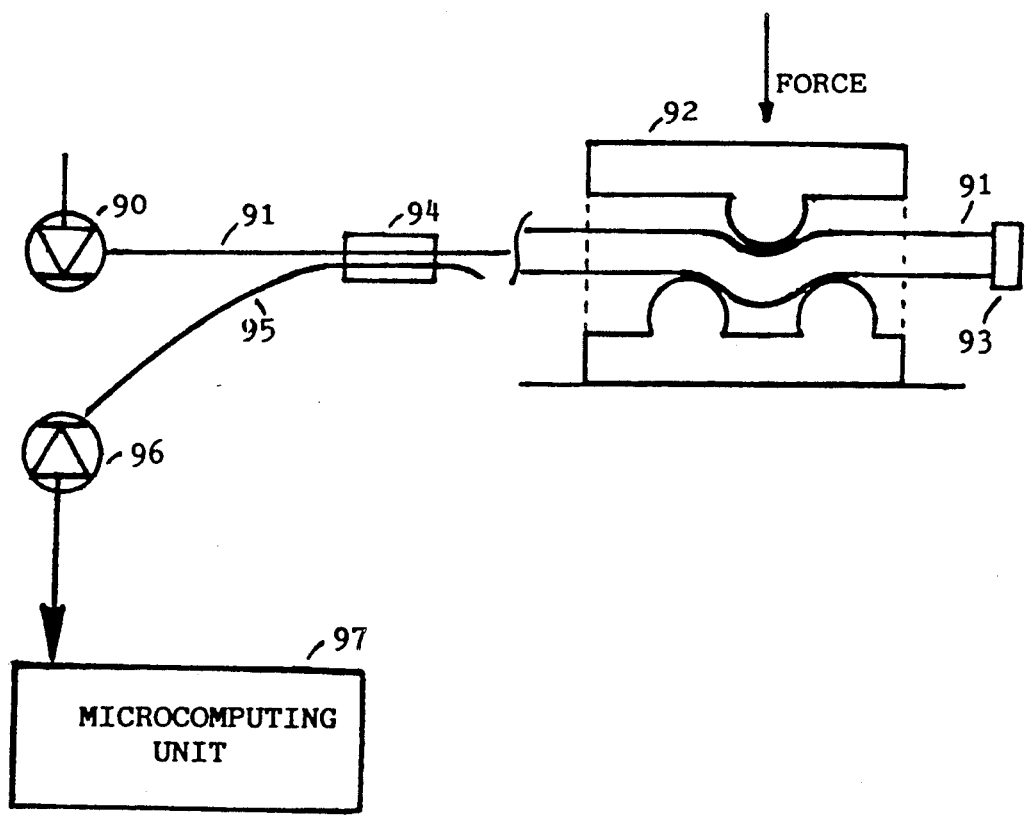
FIG. 4 illustrates an arrangement for the simultaneous measurement of temperature and pressure with a single probe.

One preferred embodiment of an arrangement for measuring both pressure and temperature with a single probe is shown in FIG. 4. A light source 90 injects interrogating light pulses of intensity $I_o$ and suitable wavelengths into an optical fiber 91 disposed within a fiber microbender 92 being acted upon by the force being measured. Attached to the distal end of the fiber is a luminescent tip 93 comprised of a material chosen from the class of materials described in section 2.0 above and FIG. 3, having an absorption band including the wavelengths of the injected light, a luminescence in response to the absorption of said light, the quantum efficiency of which is substantially invariant over the temperature range of operation of the device, and a luminescence decay time $\tau$ which is a sensitive function of temperature over the same range. Under the action of the force, the microbender 92 stresses the fiber 91 and causes an attenuation of the pulsed interrogating light of an intensity $P_o$ injected into the fiber to the attenuated intensity $P_o(1-\alpha)$, where the value of $\alpha$ is a function of the pressure applied to the microbender. The intensity of the light transmitted by the fiber under the microbender and incident on the luminescent tip 93 generates a luminescence therein with a time-averaged intensity $I_f$ which is an indicator of the pressure acting on the microbender, and is independent of temperature. On the other hand, the luminescence decay time $\tau$ of the probe is a temperature indicator, independent of the force applied to the microbender. A fraction of the intensity of the luminescence emitted by the tip 93 is collected by the same fiber 91 and directed, via fiber optic coupler 94 and the fiber segment 95, to photodetector 96. The force-dependent luminescence intensity $I_f$ received by the photodetector and the luminescence decay time $\tau$ are processed into both temperature and force readings at the microcomputing unit 97. One can thus measure both force and temperature with a single probe, a single light source and a single photodetector.

The duration of the interrogating light pulses should be preferable much shorter than the shortest decay time of the probe luminescence over the temperature range of operation of the device.

In an alternate embodiment one may use, instead of pulsed interrogation light, an AC-modulated interrogating light of a peak intensity which decays in a time shorter than the decay time of the probe luminescence.

5.0 The Measurement of Displacement and Temperature with a Single Probe

Figure 5:
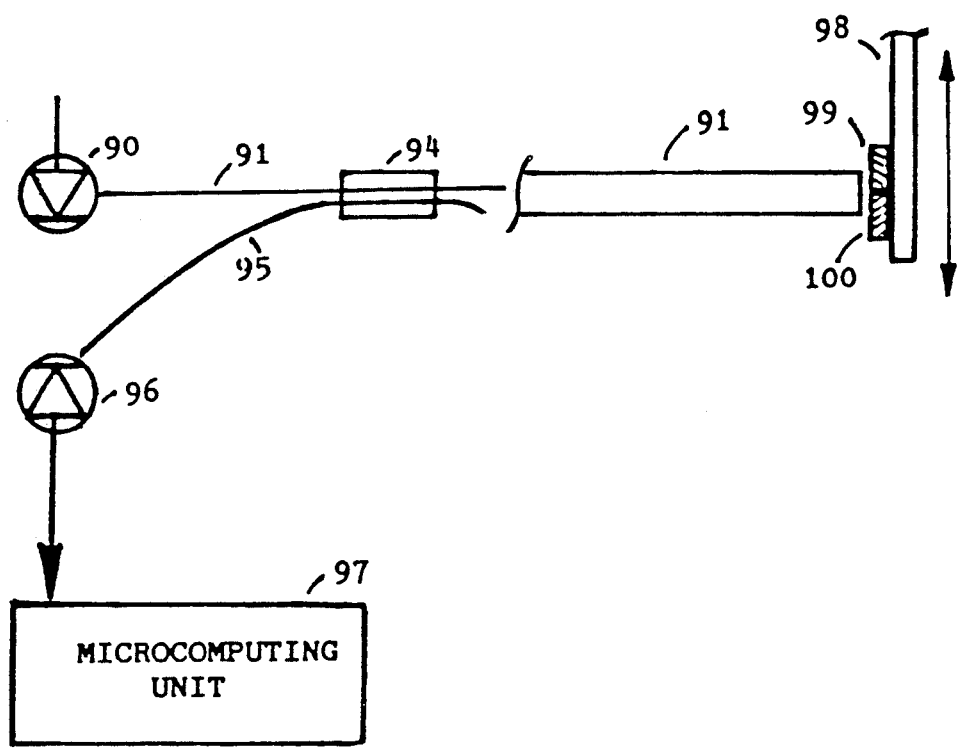
FIG. 5 illustrates an arrangement for the simultaneous measurement of temperature and position or displacement with a single probe.

The luminescent materials discussed in section 2.0 above can be used as probes for the simultaneous measurement of displacement and temperature with a single probe, or for the simultaneous measurement of temperature and any parameter which controls the position or displacement of a probe. In one preferred arrangement, illustrated in FIG. 5, the probe is a screen 98 which moves along the directions of the arrows and includes two contiguous layers 99 and 100. Layer 99 is comprised of a Cr(III)-doped photo-luminescent material, for example Cr:YAG. Layer 100 is light-reflective. Opposite the screen is the distal tip (tip opposite to the light injection tip) of the optical fiber 91 into which has been injected pulsed interrogating light beam of wavelengths within an optical absorption band of the Cr(III)-doped luminescent material of layer 99 and of a pulse duration much shorter than the luminescence decay time $\tau$ of this material. The electro-optical system is otherwise the same as that of FIG. 4. The distal tip of fiber 91 illuminates the screen 98 with an interrogating light spot, only part of the intensity of which is incident on the photoluminescent layer 99. As the screen moves, the relative intensities of the interrogating light incident on layers 99 and 100 vary as a function of the position of the screen, and the relative intensities of the light reflected from layer 100 and the time-averaged luminescence light emitted from the Cr(III)-doped layer 99 entering fiber 91 will be a function of said position. The luminescence decay time $\tau$ of layer 99 will be an accurate indicator of temperature, independent of the position or displacement of the screen.

In a simpler arrangement, one may omit the measurement of the intensity of the light reflected by the screen, as the intensity of the interrogating light incident on the luminescenct probe, and hence the time-averaged intensity $I_f$ of the probe luminescence, will vary with the position or displacement of the probe. The accuracy of the readings obtained with such arrangement may not be as high as those obtained by referencing said luminescence intensity to the intensity of the excitation light reflected by the probe, but should be sufficient for many industrial applications.

Any physical variable which can be converted into a displacement of an object can be sensed and/or measured with this technique. For example, if the screen 99 is attached to the push-rod of a pressure sensing diaphragm, then it could be used for the simultaneous measurement of both temperature and pressure.

In an alternate embodiment of the same invention, the luminescent screen is stationary and the distal tip of the optical fiber is attached to the object undergoing the displacement. The end result is the same: the intensity of the interrogating light spot incident on the luminescent material, and hence the intensity of the luminescence generated therein, varies as a function of the displacement of the object.

Since some changes may be made in the foregoing disclosure without departing from the invention herein disclosed, it is intended that all matter contained in the above description and depicted in the accompanying drawings be construed in an illustrative and not in a limiting sense.

I claim:

1. A temperature measuring arrangement comprising:
   (a) probe means including a photoluminescent material containing luminescent centers so characterized that, when excited with transient interrogating light of a wavelength or wavelengths within a pre-determined spectral range, they emit luminescence light from two excited electronic energy levels, one of them being higher than the other and having a higher rate of luminescence decay than that of said other level, the relative intensities of the luminescence light emitted from each of said two levels varying as a function of the probe means temperature, the intensity of the luminescence light emitted from said higher level increasing with increasing temperature within a pre-determined temperature range within which the quantum efficiency of the total luminescence emitted from said two levels is approximately invariant, the combined luminescence light emitted from said two levels continuing in time beyond the termination of the transient excitation light with a decay time of its intensity which decreases in a known manner with an increase in temperature within said temperature range;
   (b) a source of said interrogating light;
   (c) fiber optic means for directing said interrogating light to said probe means;
   (d) fiber optic means for directing a fraction of the intensity of the luminescence light emitted from said probe means to photodetector means; and
   (e) photodetector means for measuring the decay time of the luminescence emitted from said probe means, said luminescence decay time being an indicator of the probe means temperature.

2. A temperature measuring arrangement as claimed in claim 1, wherein said material is chosen from the group of luminescent inorganic crystalline materials comprising beryls, magnesium oxide and garnets doped with trivalent chromium or divalent vanadium.

3. A temperature measuring arrangement as claimed in claim 1 and additionally having self-checking features, wherein the wavelengths of said interrogating light are within a spectral region within which the probe absorbs only a fraction $\alpha$ of the intensity of the light incident on the probe, the value of $\alpha$ increasing with an increase in temperature as a function of the value of the so-called Boltzmann factor $\exp(-\beta/T)$, where $\beta$ is a quantity which remains substantially constant over said temperature range and T is the absolute temperature, said arrangement additionally comprising means for measuring the intensity of the luminescence light emitted by the probe and received by said photodetector means, said intensity being another indicator of the probe temperature.

4. A temperature measuring arrangement as claimed in claim 1 and additionally adapted to sense a displacement of an object, wherein said displacement varies the intensity of the interrogating light incident on said photoluminescent material at said probe means, thereby varying the intensity of said luminescence light emitted by said probe means and received by said photodetector means as a function of said displacement.

5. A temperature measuring arrangement as claimed in claim 4 and additionally adapted to measure simultaneously both temperature and a force or pressure, comprising the arrangement claimed in claim 4 wherein the position or displacement of said object is determined by the force or pressure applied on said object, and the magnitude of the force or pressure is indicated by the position or the magnitude of the displacement of said object.

6. A temperature measuring arrangement as claimed in claim 1 and additionally adapted to measure a force, wherein at least one point along said fiber optic means for directing said interrogating light to said photoluminescent probe means is under the action of the force, said force causing the attenuation of said interrogating light from an intensity $P_o$ injected into said fiber optic means to the intensity $P_o(1-\alpha)$, where $\alpha$ is a fraction of unity, the magnitude of which varies as a function of the magnitude of the force being measured, thereby causing a decrease of the intensity of the luminescence light emitted by said photoluminescent probe means, the magnitude of said decrease varying with the magnitude of the force.

7. A method for measuring temperature, comprising the steps of:
   (a) exposing a probe to the temperature to be measured, said probe including a photoluminescent material containing luminescent centers so characterized that, when excited with transient interrogating light of a wavelength or wavelengths within a pre-determined spectral range, they emit luminescence light from two excited electronic energy levels, one of them being higher than the other and having a higher rate of luminescence decay than that of said other level, the relative intensities of the luminescence light emitted from each of said two levels varying as a function of the probe temperature, the intensity of the luminescence light emitted from said higher level increasing with increasing temperature within a pre-determined temperature range within which the quantum efficiency of the total luminescence emitted from said two levels is approximately invariant, the combined luminescence light emitted from said two levels continuing in time beyond the termination of the transient excitation light with a decay time of its intensity which decreases in a known manner with an increase in temperature within said temperature range;
   (b) illuminating said probe with said interrogating light, thereby generating luminescence light emitted by the probe;
   (c) directing a fraction of the intensity of said luminescence light to photodetector means; and
   (d) measuring the decay time of said luminescence light, said decay time being an indicator of the probe temperature.

8. A method for measuring temperature as claimed in claim 7, wherein said probe contains a photo-luminescent material chosen from the group of inorganic crystalline materials including beryls, magnesium oxide and garnets doped with trivalent chromium or divalent vanadium.

9. A method for measuring temperature as claimed in claim 7 wherein the wavelengths of said excitation light are within a spectral region within which said probe has a temperature-dependent optical absorption coefficient, the method additionally comprising the measurement of the time-averaged intensity of the luminescence light received by said photodetector means, said time-averaged intensity being an additional indicator of the probe temperature.

10. A method for measuring temperature as claimed in claim 7 and additionally adapted to measure the position or displacement of an object, the method comprising the additional steps of:
  (a) providing an optical fiber into which the interrogating light is injected, the distal tip of which is adapted to illuminate said probe with a spot of interrogating light;
  (b) providing said probe in mechanical communication with said object, and so positioned relative to the distal tip of said optical fiber that the intensity of the interrogating light spot incident on said luminescent material varies as a function of the position of the probe and, hence, of said object;
  (c) thereby generating luminescence light emitted from said luminescent material, the time-averaged intensity of which is an indicator of the position of said object.

11. A method for measuring temperature as claimed in claim 7 and additionally adapted to measure the position or displacement of an object, the method comprising the additional steps of:
  (a) providing an optical fiber into which the interrogating light is injected, the distal tip of which is adapted to illuminate said probe with a spot of interrogating light;
  (b) providing said distal fiber tip in mechanical communication with said object, and so positioned relative to said probe that the intensity of the interrogating light spot incident on said luminescent material varies as a function of the position of said distal fiber tip and, hence, of said object;
  (c) thereby generating luminescence light emitted from said luminescent material, the time-averaged intensity of which is an indicator of the position of said object.

* * * * *